(12) United States Patent
Lorbiecki et al.

(10) Patent No.: US 6,626,408 B1
(45) Date of Patent: Sep. 30, 2003

(54) ADJUSTABLE LIMB SUPPORT

(75) Inventors: John E. Lorbiecki, Hubertus, WI (US); Lawrence E. Murphy, Shorewood, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/159,677

(22) Filed: May 31, 2002

(51) Int. Cl.[7] .................................................. E04G 3/00
(52) U.S. Cl. .................................................. 248/279.1
(58) Field of Search ........................... 248/118.3, 279.1, 248/118.5, 456, 454

(56) References Cited

U.S. PATENT DOCUMENTS

| | | | | |
|---|---|---|---|---|
| 3,645,501 A | * | 2/1972 | Musgrove | 254/126 |
| 4,341,042 A | * | 7/1982 | Schulz | 49/404 |
| 4,690,378 A | * | 9/1987 | Jarman et al. | 254/8 B |
| 5,074,501 A | * | 12/1991 | Holtta | 248/118.3 |
| 6,454,224 B1 | * | 9/2002 | Nogueira | 248/118.5 |

* cited by examiner

Primary Examiner—Leslie A. Braun
Assistant Examiner—Kofi Schulterbrandt
(74) Attorney, Agent, or Firm—Joseph S. Heino; Carl B. Horton

(57) ABSTRACT

An adjustable limb support includes a hinged vertical support trough that is movable about a central pivot post and is attached to a pair of hinged support arms, the hinged support arms being horizontally adjustable at one end to allow for vertical height adjustment at the other end. The limb support is configured to be adjustable yet fixable in an infinite number of positions. The limb support is also intended to be radio transparent for use in CT, x-ray and PET applications.

19 Claims, 5 Drawing Sheets

ADJUSTABLE LIMB SUPPORT

FIELD OF THE INVENTION

This invention relates to a limb supporting device that is intended to be used in conjunction with radiographic diagnostic procedures. More particularly, it relates to an adjustable limb support for use while a patient is undergoing radiological examination wherein the limb support allows for multiple and reproducible elevational and rotational settings and adjustments relative to the limb that is being supported by the holder. It also relates to such a limb support that is generally radiolucent.

BACKGROUND OF THE INVENTION

Radiological examinations often require a part of a patient's anatomy to be positioned and remain held in a certain position that is either extremely uncomfortable to the patient, exhausting to the patient or physically impossible for the patient to hold for the duration of the examination. Many methods and devices for positioning limbs and extremities for examination are currently used, from formed pillows to mechanical devices. Generally speaking, devices designed to support parts of the human body in various positions must provide rigid support in addition to providing a comfortable, or at least tolerable, experience for the patient. Devices designed to support parts of the human body must further provide a broad range of adjustability so that they can accommodate a broad range of sizes and shapes of people. It is also desirable to design such devices so that the position of the particular part of the human anatomy being examined can be duplicated or recreated if repeat examination becomes necessary due to poor quality of the radiographic image.

For example, the magnetic resonance imaging ("MRI") study of the human shoulder requires a patient to elevate his or her arm and hold the arm in various positions for the duration of the examination. At the same time, those generally in need of an MRI study may also have some sort of injury to the shoulder and may experience great difficulty holding any position on his or her own for an extended period of time. On the other hand, the MRI machine requires the patient to remain very still in order to capture and produce a high quality image. The device of the present invention is designed to provide a comfortable support mechanism for patients undergoing this type of examination and is also designed to adapt to provide limb support of other types for patients undergoing other similar exams.

Accordingly, it is an object of the present invention to provide a limb support for use with an imaging machine. It is another object of the present invention to provide a limb support of the foregoing type that is capable of multiple adjustments. It is yet another object of this invention to provide a limb support of the foregoing type that, while adjustable, is capable of reproducing a limb position setting for radiographic studies. It is still another object of this invention to provide a limb support of the foregoing type that is generally radiolucent and results in improved radiographic imaging. The foregoing and other objects and advantages of the invention will be apparent from the following summary and detailed description.

BRIEF SUMMARY OF THE INVENTION

The limb support of the present invention consists of a hinged vertical support that permits movement of the subject in the Y-axis, a center pivot post that allows 360-degree rotation in the Z-axis and rotation in the X-axis. One end of the hinged support is firmly mounted to a base. The other end of the hinged support is adjustable along the base to allow vertical adjustment of the subject to be obtained. Together, the supports form an apex at which the hinge is located. The hinge is also the mounting point for a limb support trough. The hinge provides a mounting point for the limb support trough as well as providing a point of pivot and rotation for the limb support trough.

The limb support is a "purpose formed" device that is designed to support the limb as well as hold it in position so that an accurate image can be created. Material selection for the entire device is modality specific, with non-magnetic materials required for MRI and X-ray and transparent materials being required for CT, X-ray, and PET.

The advantages of the limb support of the present invention are apparent from a brief examination of the device itself. For example, the limb support permits virtually unlimited adjustment in the vertical axis and has excellent rigidity when positioned. Also, the pivoting limb support "matches" the location of the limb for patient comfort. Perhaps even more important is the ability of an experienced technician or radiologist to repeat the patient's limb position within the MRI machine as closely as possible. As is obvious, the limb support of the present invention is very simple in design. This simplicity in design results in the apparatus having a very high degree of reliability. Also, the apparatus of the present invention is very cost-effective insofar as the limb support is both adjustable and can be changed to accommodate various body parts and positions. Lastly, the apparatus of the present invention is designed to incorporate existing radiolucent materials which will improve image quality and reduce the need for repeat studies.

DETAILED DESCRIPTION

Figure 1:
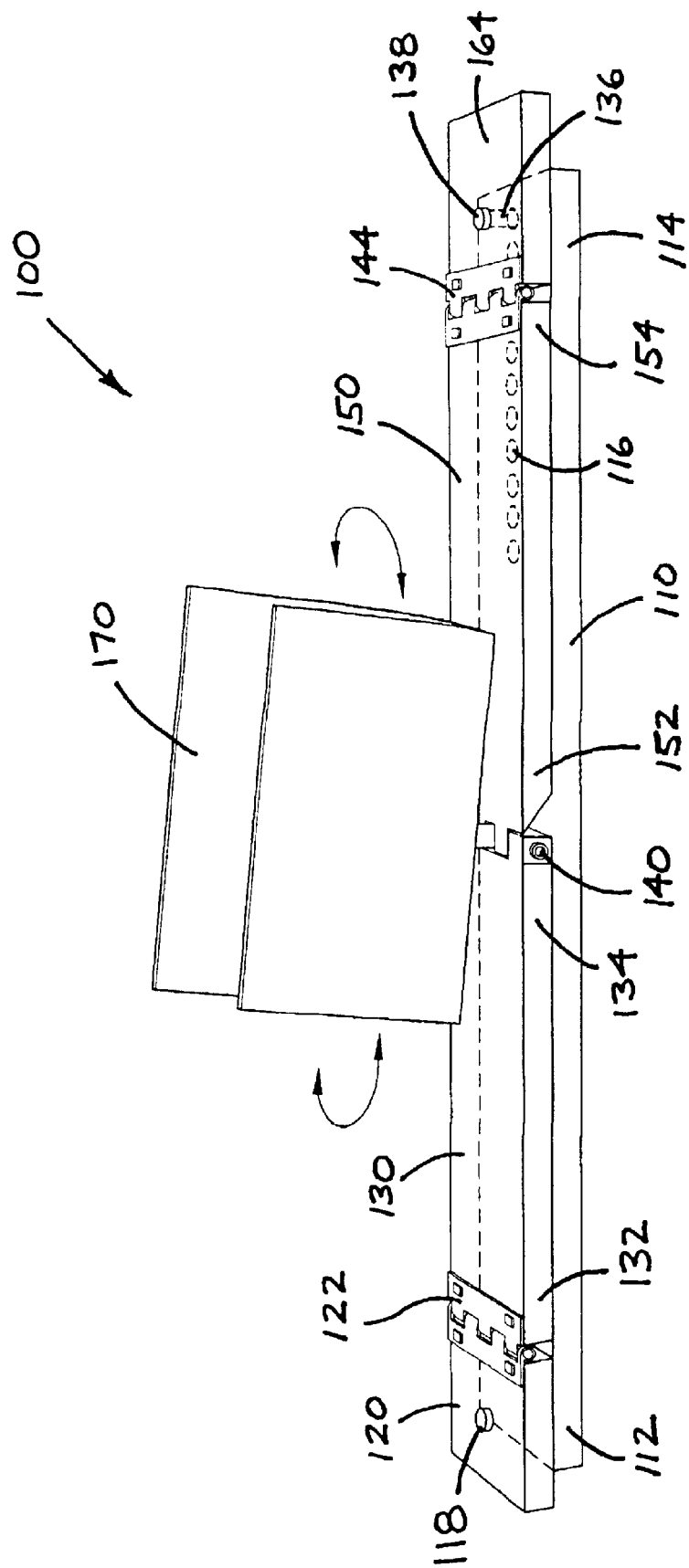
FIG. 1 is a front and top perspective view of one embodiment of a limb support constructed in accordance with the present invention and showing the support in a fully "down" position.

Referring now to the drawings in detail, wherein like numbered elements correspond to like elements throughout, FIG. 1 is view of one embodiment of the adjustable limb support (generally identified 100) constructed in accordance with the present invention. Although illustrated in a particular embodiment for purposes of this detailed description, it is to be understood that alternative embodiments could be devised without deviating from the scope of the disclosure herein. In general, however, the adjustable limb support of the present invention includes four main elements. The first main element is a base 110, which base 110 provides a stable platform for mounting the second and third main elements, a first scissor arm 130 and a second scissor arm 150, respectively. The first scissor arm 130 and the second scissor arm 150 are effectively joined together at one end 134, 152, respectively, by means of a top hinge 140. The top hinge 140 provides an attachment for the fourth main element, a generally U-shaped limb support trough 170.

In more detail, the base 110 of the device 100 of the present invention is in the general shape of an elongated rectangle. In one embodiment of the device 100, a first mounting plate 120 is secured at a first end 112 of the base 110. The mounting plate 120 can be secured to the base 110 by using nearly any means of attachment including adhesive, clamp, Velcro® brand fastener, screws or rivets so long as the mounting means does not permit rotation or translation of the mounting plate 120 relative to or with respect to the base 110. In the embodiment shown in FIG. 1, the base 110 and the first mounting plate 120 each have a cooperating and complementary aperture that aligns to accommodate a locating peg 118 therewithin. Although not shown, it is to be understood that either the base 110 or the mounting plate 120 could feature a series of such apertures to allow adjustability of the first mounting plate 120 with respect to the base 110.

In the illustrated embodiment, the second end 114 of the base 110 features a plurality of regularly spaced apertures 116 disposed in a generally linear pattern. The apertures 116 should be marked such that an operator of the diagnostic equipment can duplicate a patient's position in successive examinations by reference to such markings. In this manner, the radiologist and the treating physician will be able to compare previous images with more recent images and know that the images are of the same part of the body taken in the same relative position. See FIGS. 4 and 5.

Figure 2:
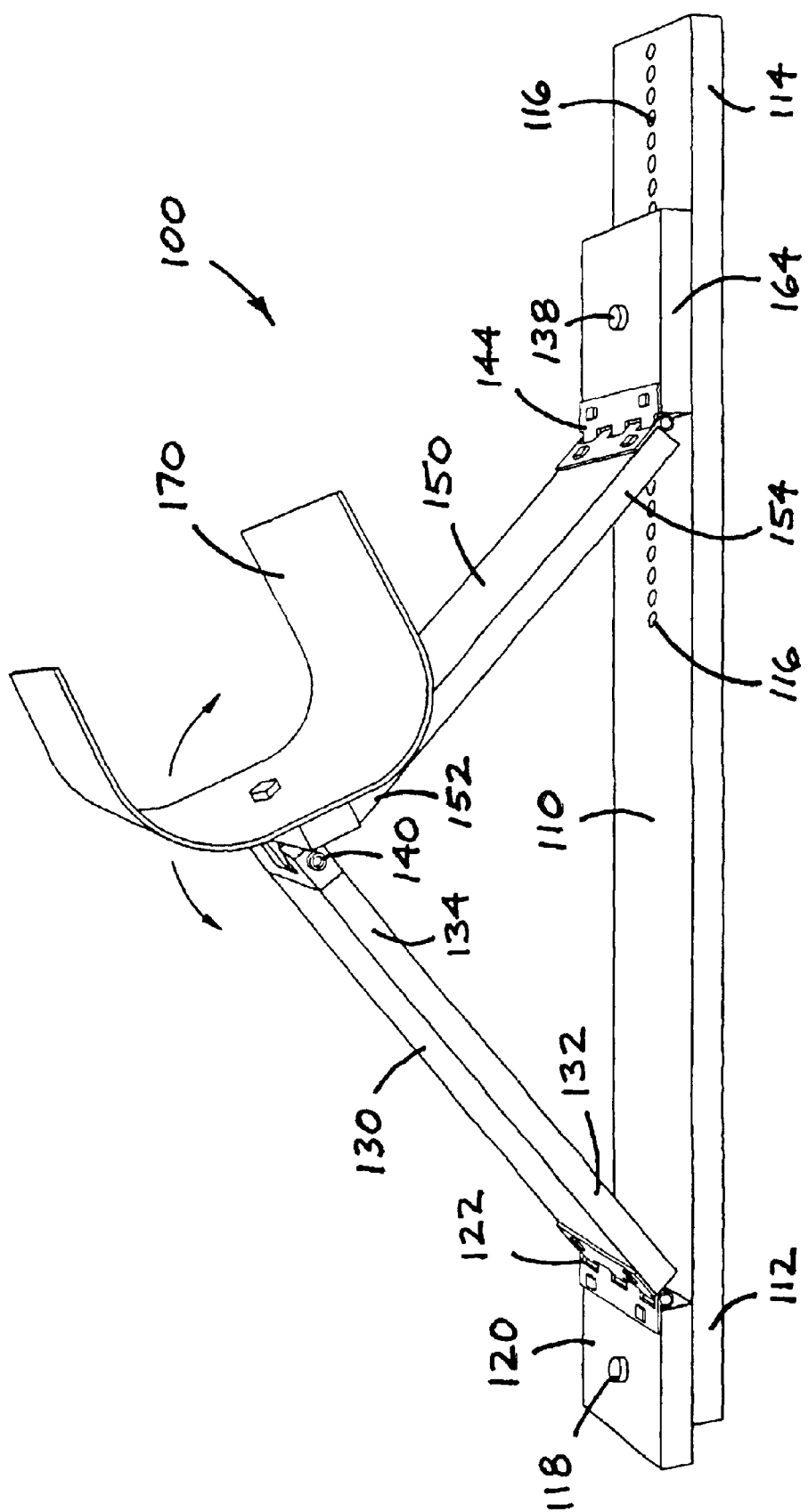
FIG. 2 is a front and top perspective view of the limb support shown in FIG. 1 and showing the support in a somewhat elevated position.

The mounting plate 120 provides an attachment and pivot point for the first scissor arm 130. The first end 132 of the first scissor arm 130 is mounted to a first hinge 122. This first hinge 122 is attached to the top of the mounting plate 120. In this fashion, the first hinge 122 permits upward rotation of the first scissor arm 130 with respect to the base 110. Although shown as a separate component, it is to be understood that the hinge 122, or any other hinge used in this device 100, could be a "living hinge" and machined into the adjoining elements between which the hinge 122 is functionally disposed. The second end 134 of the first scissor arm 130 is attached to the top hinge 140. The top hinge 140 connects the first scissor arm 130 to the second scissor arm 150 and allows rotation of the first scissor arm 130 relative to the second scissor arm 140. See FIG. 2.

The first end 152 of the second scissor arm 150 is attached to the top hinge 140. The second end 154 of the second scissor arm 150 is attached to yet another hinge, a sliding hinge 144. The sliding hinge 144 is attached to a sliding mounting plate 164. The sliding hinge 144 allows rotation of the second scissor arm 140 relative to the sliding mounting plate 164. The sliding mounting plate 164 is generally rectangular in shape and moves or "slides" longitudinally along the base 10. The sliding mounting plate 164 has an aperture 136 of similar size and shape to the apertures 116 defined within that end 114 of the base 110. A locking peg 138 is provided to secure the sliding mounting plate 164 to the base 110. In application, and as the sliding mounting plate 164 is moved towards the fixed mounting plate 120, the apex formed at the point of the top hinge 140 is variably elevated. See FIG. 2. Conversely, moving the sliding mounting plate 164 away from the fixed mounting plate 120 lowers the apex. Here again, although a peg 138 and a plurality of apertures 116, 136 with which it functionally cooperates are shown, it is to be understood that any method of releasable securement could be incorporated by design and still come within the scope and intended purpose of the present invention.

Figure 3:
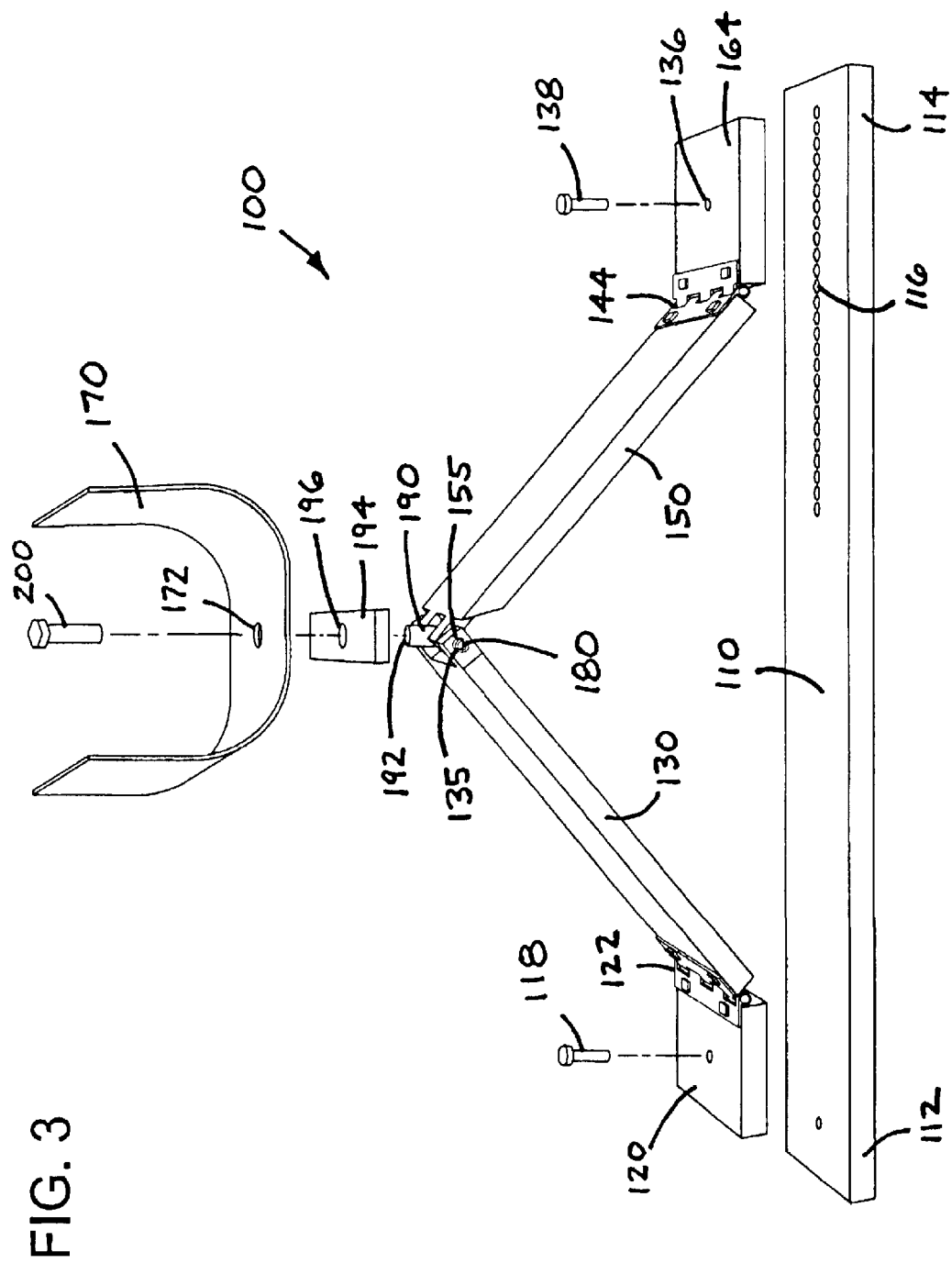
FIG. 3 is a front and top perspective view of the limb support embodiment illustrated in FIG. 1 and showing the elements thereof in an exploded spatial relationship.
Figure 4:
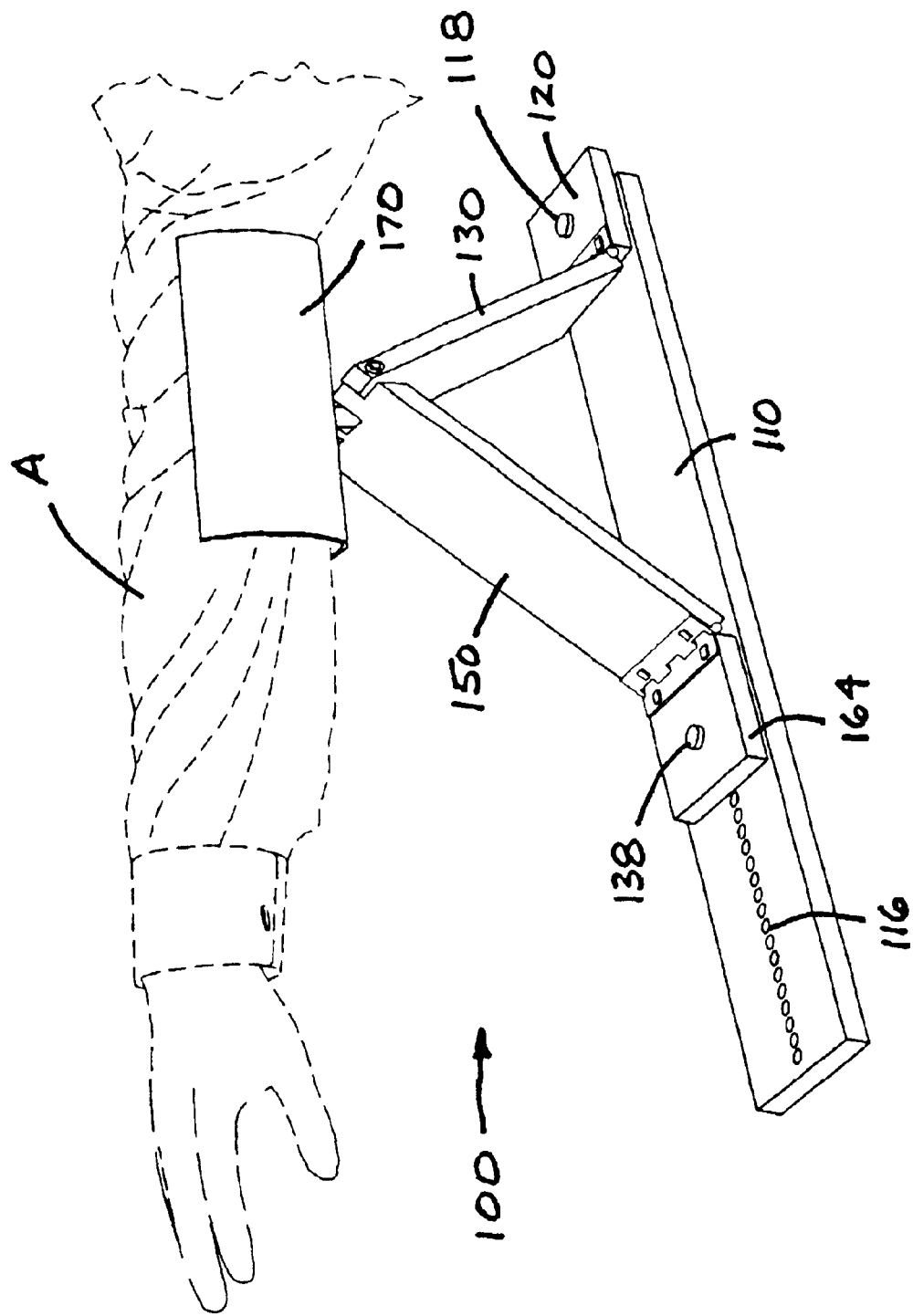
FIG. 4 is a front, top and left side perspective view of the limb support embodiment shown in FIG. 1 and showing a patient's arm in phantom view in the fully elevated position.
Figure 5:
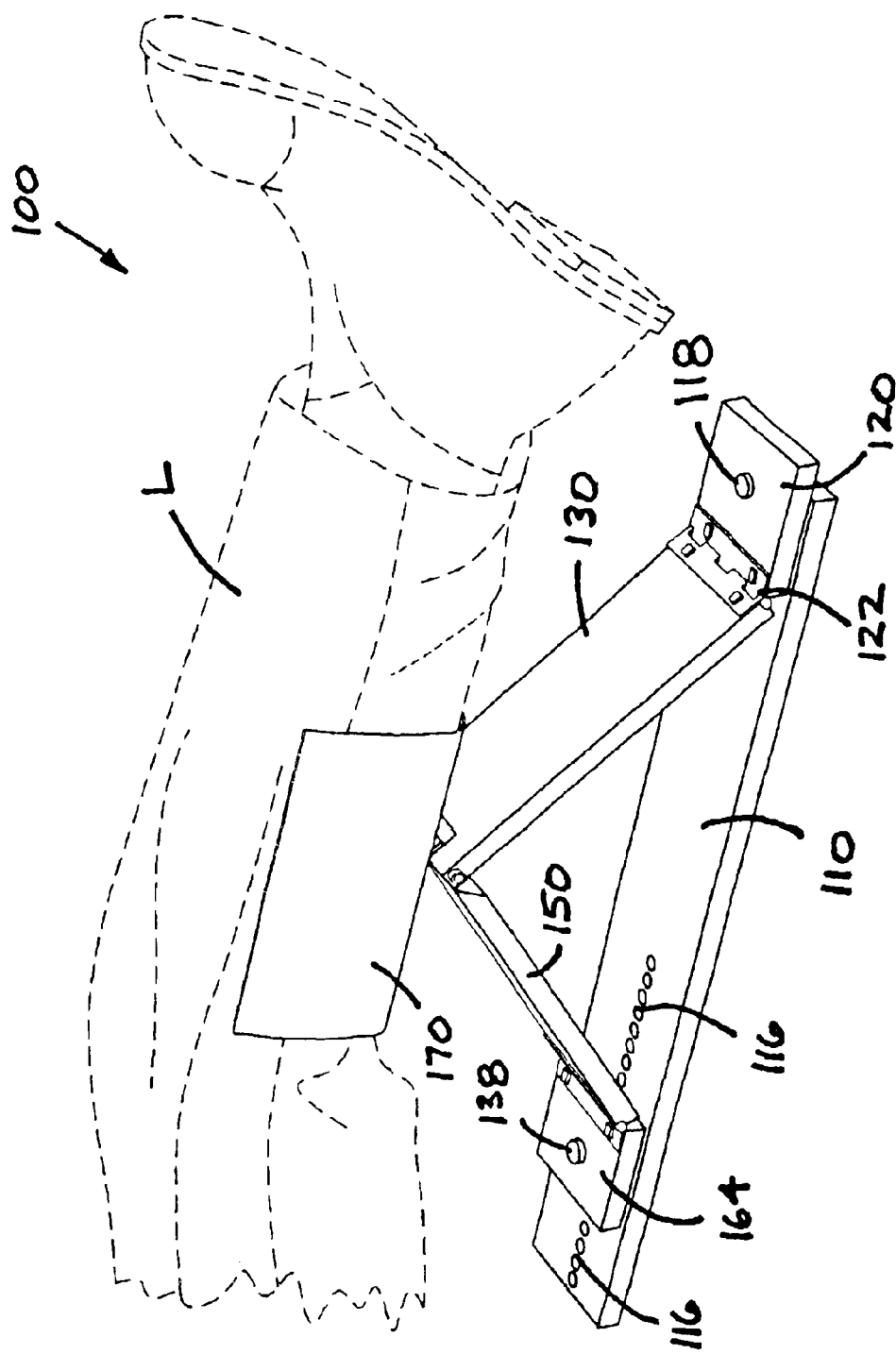
FIG. 5 is a front, top and right side perspective view of the limb support embodiment illustrated in FIG. 1 and showing a patient's leg in phantom view in a somewhat elevated position.

With special regard to FIG. 3, an exploded view of the illustrated embodiment of the present invention shows a detailed view of the top hinge 140. The top hinge 140 may employ a rod 180 that slides through a set of cooperative and co-linear apertures 135, 155 defined within each of the first and second scissor arms 130, 150, respectively. Also provided is a central support bracket 190. The central support bracket 190 provides a perpendicularly oriented aperture (not shown) that is also aligned with and is co-linear to the apertures 135, 155 of the first and second scissor arms 130, 150 to allow passage of the rod 180 therethrough. Alternatively, the support bracket 190 may simply be mounted on the rod 180 using some type of fastener. As shown, a trough support plate 194 is also provided. The support bracket 190 generally provides a second axial aperture 192 thereby allowing the bracket 190 to receive a pin 200 that is aligned through a trough aperture 172 and a trough plate aperture 196 such that the limb support trough 170 is permitted to rotate 360 degrees. Further, the support bracket 190 permits the limb support trough 170 to be angled as such is desired or required with respect to the first and second scissor arms 130, 150, respectively. See FIG. 2. The limb support 100 may support a patient's arm A or leg L as shown in FIGS. 4 and 5, for example.

The limb support trough 170 shown is designed to accommodate a wide variety of patients. The limb support 170 may also be purpose-built for specific applications. For example, a shoulder MRI study often requires a patient to hold an arm at a forty-five degree angle outwardly and at a forty-five degree angle upwardly relative to his or her body axis when the patient is laying on his or her back. In a case such as this, a limb support 100 could be readily be adjusted so that the patient's upper arm is supported and the patient's lower arm is comfortably held out in front of the patient. Another limb support trough 170 configuration might represent a ninety degree bend to fully support the patient's arm and forearm. This particular embodiment might also be used for a patient with an injured knee, to hold the knee in a fixed, but comfortable position for imaging. The limb support trough 170 is designed to rotate azimuthally 360° about its axis. It is additionally able to pivot such that it allows the user to adjust the angle of the limb support trough 170 relative to the first 130 and second 150 scissor arms. It is envisioned by the inventors that both the angle of pivot and the degree of rotation of the limb support trough 170 may both be measured from the device and recorded for future reference. The degree of rotation of the limb support trough 170 can be measured using a circular disk with degree markings. This value can then be recorded and the next time the patient is imaged, the operator can reposition the patient precisely as before. The angle of pivot can also be recorded, either from the vertical or relative to either the first 130 or second 140 scissor arms. In the case of both the angle of pivot and the degree of rotation, the inventors also envision using a "memory" type joint. In other words, the joint will be stiff enough such that the weight of the patient's limb should not cause movement but the joint is at the same time loose enough to permit movement of the limb support when it is moved by the operator. Alternatively, the inventors envision a fixable joint. This type of joint provides greater ease of movement but requires one to tighten a bolt to secure the angle of rotation or pivot of the limb support.

The above described parts can be made of nearly any material but a radiolucent material is preferred. Only a radiolucent material will provide clear and accurate images for the person reading the image.

With only these above described elements, the inventors have created a new, versatile and unique apparatus for holding a patient's arm or leg during a diagnostic examination. This new and unique device allows the operator to adjust the patient's position with six degrees of freedom. The apparatus has nearly infinite vertical adjustment using the first and second scissor arms. Additionally, the device of the present invention allows the limb support 360 degrees of rotation. Further, the angle the limb support makes with respect to the first and second scissor arm can be adjusted. Even more flexibility can be offered through use of removable and interchangeable limb supports. For example, limb supports can be designed to accommodate both arms and legs or to accommodate either an arm or a leg but to adjust and hold the limb in a specified position.

Parts List

| Parts List: | |
|---|---|
| Part Name | Part Number |
| Adjustable limb support | 100 |
| Base | 110 |
| First end of the base | 112 |
| Second end of the base | 114 |
| Apertures in base | 116 |
| Locating peg | 118 |
| First mounting plate | 120 |
| First hinge | 122 |
| First scissor arm | 130 |
| First end of the first scissor arm | 132 |
| Second end of the first scissor arm | 134 |
| Aperture in first scissor arm | 135 |
| Aperture in sliding mounting plate | 136 |
| Locking peg | 138 |
| Top hinge | 140 |
| Sliding hinge | 144 |
| Second scissor arm | 150 |
| First end of the second scissor arm | 152 |
| Second end of the second scissor arm | 154 |
| Aperture in second scissor arm | 155 |
| Sliding mounting plate | 164 |
| Limb support trough | 170 |
| Trough aperture | 172 |
| Rod | 180 |
| Central support bracket | 190 |
| Second axial aperture | 192 |
| Trough plate aperture | 196 |

Based on the foregoing, we claim as our invention:

1. An adjustable limb support comprising
   a base,
   a first scissor arm,
   means for permitting rotation of the first scissor arm relative to said base,
   a second scissor arm,
   a sliding mounting plate,
   means for alternatively permitting movement and preventing movement of the sliding mounting plate with respect to the base,
   means for permitting rotation of the second scissor arm relative to said sliding mounting plate,
   means for rotatable connecting the first scissor arm to the second scissor arm at an apex, and
   a limb support trough mounted at the point of the apex formed by the first scissor arm an the second scissor arm,
   wherein rotation of the first scissor arm towards the second scissor arm moves the apex away from the base and rotation of the first scissor arm away from the second scissor arm moves the apex toward the base and wherein the adjustable limb support is comprised solely of radiolucent materials.

2. The adjustable limb support of claim 1 wherein the limb support trough consists of a generally flat bottom having two generally parallel upturned sides.

3. The adjustable limb support of claim 1 wherein the limb support trough comprises a generally U-shaped element.

4. The adjustable limb support of claim 1 wherein the angle of the limb support trough is variably adjustable relative to the horizontal when the base lies in a substantially horizontal plane.

5. The adjustable limb support of the claim 1 wherein the angle of rotation of the limb support trough is variably adjustable.

6. The adjustable limb support of claim 4 wherein the angle of the limb support trough can be fixed.

7. The adjustable limb support of claim 5 wherein the angle of rotation of the limb support trough can be fixed.

8. An adjustable limb support comprising
   a longitudinally extending base, said base having a first end and a second end,
   a first mounting plate, said first mounting plate being removably attachable to the first end of said base,
   a first scissor arm, said first scissor arm having a first end and a second end,
   means for rotatably connecting the first end of the first scissor arm to said mounting plate,
   a second scissor arm, said second scissor arm having a first end and a second end,
   means for rotatably connecting the second end of the first scissor arm to the second end of said second scissor arm,
   a second mounting plate, said second mounting plate being movable longitudinally along the base,
   means for rotatably connecting the first end of the second scissor arm to said second mounting plate,
   means for fixably adjusting the position of the second mounting plate with respect to the first mounting plate along the base,
   a limb support trough mounted between the first scissor arm and the second scissor arm, and
   means for permitting rotation of the limb support trough about a vertical axis and relative to the horizontal.

9. The adjustable limb support of claim 8 wherein the base includes a plurality of regularly-spaced apertures arranged linearly defined within it, the second mounting plate has a single aperture defined within it, and a locating device is inserted through the aperture in the second mounting plate and into the base such that the first and second scissor arms form a generally triangular relationship with the base.

10. The adjustable limb support of claim 8 wherein the means for permitting rotation between the first mounting plate and the first scissor arm, the first scissor arm and the second scissor arm, and the second scissor arm and the second mounting plate comprises a hinge.

11. The adjustable limb support of claim 8 wherein the adjustable limb support may be constructed entirely of nonmagnetic and/or radiolucent material.

12. The adjustable limb support of claim 8 wherein the angle of the limb support trough relative to the horizontal can be fixed.

13. The adjustable limb support of claim 8 wherein the angle of rotation of the limb support trough can be fixed.

14. An adjustable limb support comprising a base having a first end and a second end and a plurality of regularly spaced apertures arranged linearly, a mounting plate affixed to the first end of the base, a first scissor arm having a first end and a second end, a first hinge having a first end affixed to the mounting plate and a second end affixed to the first scissor arm, said first hinge permitting angular rotation of the first scissor arm with respect to the base, a second scissor arm having a first end and a second end, a top hinge having a first end affixed to the first scissor arm and a second end affixed to the second scissor arm and an aperture, said top hinge permitting rotation of the second scissor arm with respect to the first, a sliding mounting plate having a central aperture similar in size and shape to said apertures in said base, a second hinge having a first end attached to the second end of the second scissor arm and a second end attached to the sliding mounting plate, a locating device long enough to be inserted through the sliding mounting plate and into the apertures in the base to secure the position of the sliding mounting plate to the base, and a limb support having a pin below it designed to slide into the top hinge wherein the limb support is permitted to rotate with respect to the first and second scissor arms, wherein the locating device is inserted through the aperture in the sliding mounting plate and into the base such that the first and second scissor arm form a generally triangular relationship with the base, and wherein the adjustable limb support is constructed entirely of a radiolucent material.

15. The adjustable limb support of claim 14 wherein the limb support permits changes in its angular orientation with respect to the first and second scissor arm.

16. A limb support assembly comprising a generally flat, longitudinally extending base, said base having a first end and a second end and a plurality of regularly spaced apertures arranged linearly alone said base, a generally flat mounting plate affixed to the first end of the base, a generally flat, longitudinally extending first scissor arm, said first scissor arm having a first end and a second end, means for hingedly attaching the mounting plate to the first scissor arm thereby permitting angular rotation of the first scissor arm with respect to the base, a generally flat, longitudinally extending second scissor arm, said second scissor arm having a first end and a second end, means for hingedly attaching the first scissor arm to the second scissor arm thereby permitting rotation of the second scissor arm with respect to the first scissor arm, a sliding mounting plate having a central aperture similar in size and shape to said apertures in said base, means for hingedly attaching the second end of the second scissor arm to the sliding mounting plate thereby permitting rotation of the second scissor arm with respect to the sliding mounting plate, a locating device long enough to be inserted through the sliding mounting plate and into the apertures in the base to secure the position of the sliding mounting plate to the base, wherein the locating device is inserted through the aperture in the sliding mounting plate and into the base such that the first and second scissor arms form a generally triangular relationship with the base, a limb support, and means for rotatably mounting said limb support to said assembly at the point of the hinged attachment means between said first and second scissor arms, wherein the adjustable limb support is constructed entirely of a radiolucent material.

17. The limb support assembly of claim 16 wherein the limb support permits changes in its angular orientation with respect to the first and second scissor arm.

18. A limb support assembly comprising a generally flat, longitudinally extending base, said base having a first end and a second end, a generally flat, longitudinally extending first scissor arm, said first scissor arm having a first end and a second end, means for hingedly attaching the first scissor arm to the base thereby permitting angular rotation of the first scissor arm with respect to the base, a generally flat, longitudinally extending second scissor arm, said second scissor arm having a first end and a second end, means for hingedly attaching the first scissor arm to the second scissor arm thereby permitting rotation of the second scissor arm with respect to the first scissor arm, a sliding mounting plate, said sliding mounting plate being fixable along the length of said base, means for hingedly attaching the second end of the second scissor arm to the sliding mounting plate thereby permitting rotation of the second scissor arm with respect to the sliding mounting plate, a limb support, and means for rotatably mounting said limb support to said assembly at the point of the hinged attachment means between said first and second scissor arms wherein the adjustable limb support is constructed entirely of a radiolucent material.

19. The limb support assembly of claim 18 wherein the limb support permits changes in its azimuthally angular orientation with respect to the base and with respect to the horizontal.

* * * * *